US006324417B1

(12) United States Patent
Cotton (10) Patent No.: US 6,324,417 B1
(45) Date of Patent: Nov. 27, 2001

(54) METHOD FOR MEASUREMENT OF SKIN HISTOLOGY

(75) Inventor: Symon D'Oyly Cotton, Sycamores (GB)

(73) Assignee: Optiscan Limited (GB)

( * ) Notice: Subject to any disclaimer, the term of this patent is extended or adjusted under 35 U.S.C. 154(b) by 0 days.

(21) Appl. No.: 09/314,751

(22) Filed: May 19, 1999

Related U.S. Application Data (63) Continuation of application No. PCT/GB97/03117, filed on Nov. 19, 1997.

(51) Int. Cl.$^7$ ...................................................... A61B 6/00
(52) U.S. Cl. ............................................................ 600/475
(58) Field of Search .................................. 600/473–477; 250/338.1, 339.11; 356/448; 382/128

(56) References Cited

U.S. PATENT DOCUMENTS

| | | |
|---|---|---|
| 5,079,698 | 1/1992 | Grenier et al. . |
| 5,349,961 * | 9/1994 | Stoddart et al. ...................... 600/473 |
| 5,353,790 * | 10/1994 | Jacques et al. ...................... 600/473 |
| 5,440,388 | 8/1995 | Erickson . |
| 5,836,872 * | 11/1998 | Kenet et al. .......................... 600/306 |
| 6,081,612 * | 6/2000 | Gutkowicz-Krusin et al. ..... 382/128 |

FOREIGN PATENT DOCUMENTS

| | | |
|---|---|---|
| 2196187 | 2/1996 | (CA) . |
| WO90/13091 | 11/1990 | (WO) . |
| WO94/16622 | 8/1994 | (WO) . |
| WO96/14795 | 5/1996 | (WO) . |

OTHER PUBLICATIONS

Kini Dhawan, "Three–Dimensional Imaging and Reconstruction of Skin Lesions", Comput Med Imaging Graph May –Jun.; 1992 16(3): 153–61.*

The Role of Skin Optics in Diagnostic and Therapeutic Uses of Lasers, S.L. Jacques, Laser Biology Research Laboratory, University of Texas 1991.

Symon D'O Cotton, "Do all humans skin colours lie on a define surface within LMS space?", University of Birmingham Technical Report, Dec. 30, 1995.*

Clark et al., "the histogenesis and biologic behavioar of primary human malignant melanomas of the skin", Cancer Research 29, 705–729, Mar. 1969.*

CD Neville, "Melanoma: Issues of importance to the clinician", British Journal of Hospital Medicine, Mar. 1985.*

SL Jacques, "the role of skin optics in diagnostic and therapeutic uses of lasers", Lasers in Dermatology, 1991, pp. 1–21, XP000607863.*

* cited by examiner

*Primary Examiner*—Brian L. Casler
(74) *Attorney, Agent, or Firm*—Michael Best & Friedrich LLP (57) ABSTRACT

A method and apparatus for non-invasively measuring skin structure. Infrared radiation over an area of skin under investigation is measured to give an indication of the variation in papillary dermis thickness over said area, and the skin color coordinates at a plurality of locations over the same area of skin is also measured. The data obtained is used to calculate corrected skin color coordinates over the area corresponding to a predetermined papillary dermis thickness. The corrected skin color coordinates so obtained are compared with a reference color coordinate range for healthy skin of the same predetermined papillary dermis thickness. At an abnormal region, where the corrected skin color coordinates lie outside the reference color coordinate range, the depth of penetration of dermal melanin can be measured.

21 Claims, 4 Drawing Sheets

METHOD FOR MEASUREMENT OF SKIN HISTOLOGY

This appln is a con't of PCT/GB97/03117 filed Nov. 19, 1997.

This invention relates to a method for the non-invasive measurement of skin histology and is particularly, but not exclusively, concerned with a method for identifying and measuring the presence and depth of dermal invasion of melanin. The presence and extent of dermal invasion within a skin cancer is considered to be the most important factor governing a patient's prognosis. The present invention is considered to be potentially useful for the preliminary screening of patients to identify those who should be referred to an appropriate clinician for diagnosis and further to assist the clinician in diagnosis.

The present invention is based on the findings reported by Symon D'O Cotton in "Do all human skin colours lie on a defined surface within LMS space", University of Birmingham Technical Report, Dec. 30, 1995. The disclosure of such Technical Report is included herein by reference. In this Technical Report, the relation between healthy skin and the colour of the skin represented in LMS, a particular colour space, is reported, and is discloses that, for healthy skin, the coloration, regardless of race or amount of tanning, lies on a defined curved surface within a three-dimensional colour space. This, if used with a correct colour measurement system, can measure and quantify the amount of melanin and blood at any particular point at which this measurement is made. If the skin is sampled as an image, then corresponding images showing the variation of blood and melanin across the skin can be obtained. In the above Technical Report, it is disclosed that melanin can sometimes penetrate into the dermis producing the characteristic hues of melanoma and that this melanocytic descent has been quantified by Clark et al ("The Histogensis and Biological Behaviour of Primary Human Malignant Melanomas of the Skin", Cancer Research, 29, 1989) into five levels of tumour invasion, in which level 1 corresponds to confinement within the epidermis, level 2 corresponds to invasion into the papillary dermis, etc. In an alternative system, the extent of tumour invasion in mm from the cornified layer is expressed as the Breslow thickness. The above Technical Report also acknowledges that, in the case of melanoma, C. D. Neville ("Melanoma: Issues of Importance to the Clinician", British Journal of Hospital Medicine, Mar. 1985) discloses the existence of a strong relationship between this level of invasion and prognosis. However, the above Technical Report does not disclose in detail any method suitable for taking the necessary measurements.

According to the present invention, there is provided a method of non-invasively analysing skin structure, comprising the steps of:
(i) measuring infrared radiation from a plurality of locations over an area of skin under investigation so as to give an indication of the variation in papillary dermis thickness over said area;
(ii) measuring the skin colour coordinates at a plurality of locations over said area of skin;
(iii) using data obtained in measuring steps (i) and (ii) to calculate corrected skin colour coordinates over said area which corresponds to a predetermined papillary dermis thickness, and;
(iv) comparing the corrected skin colour coordinates obtained in step (iii) with a reference colour coordinate range for healthy skin of the same predetermined papillary dermis thickness.

The method can be used for locating and measuring the properties of a skin abnormality, in which case the method further comprises the steps of;
(v) identifying an abnormal location (i.e. a region where melanin exists within the dermis) within said area of skin where the corrected skin colour coordinates lie outside the reference colour coordinate range;
(vi) calibrating the corrected skin colour coordinates of said abnormal location with the corrected skin colour coordinates of at least one skin location having colour coordinates lying within said reference colour coordinate range for normal skin, and;
(vii) using the skin colour coordinates to assess the degree of abnormality of said abnormal skin location.

It is to be understood that using this method, it is possible to reconstruct a full 3 D model of the skin architecture which conveys information grossly comparable to the available through microscopical examination of biopsied skin tissue.

It has been found that the papillary dermal skin thickness can change markedly with some skin lesions which are not otherwise of concern. This throws the coloration of the skin off the surface of predicted coloration and so can give rise to false measurements of the histology of such skin lesions. It is for this reason that papillary dermis thickness is measured first, and subsequent calculations are based on the skin colour coordinates corrected to a predetermined papillary dermis thickness. Any arbitrary value for this thickness may be chosen, such as $2.0 \times 10^{-4}$ m which is the average value for healthy human skin.

Figure 1:
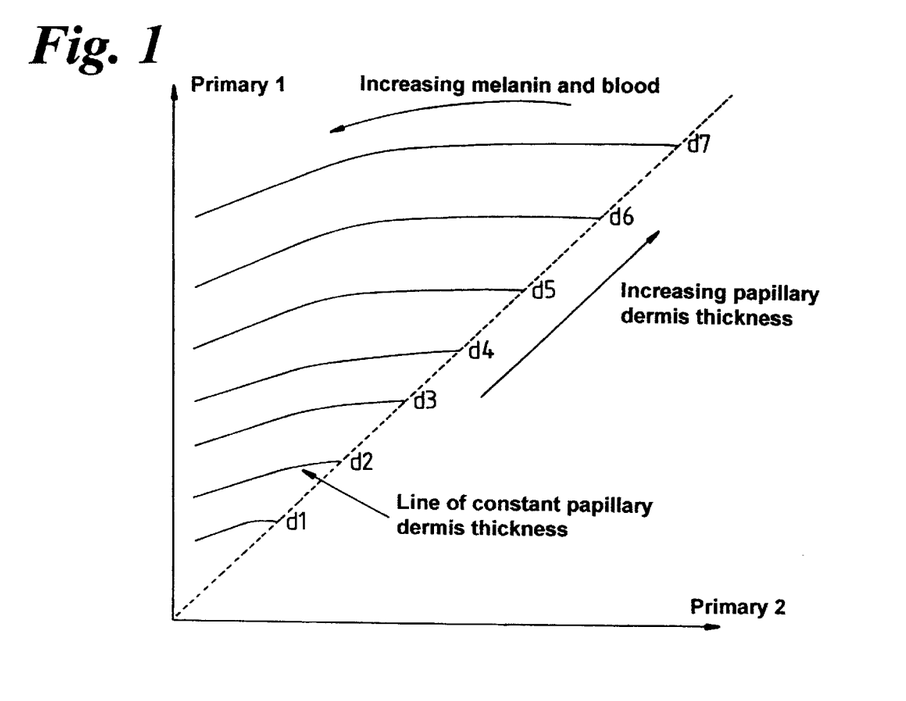
FIG. 1 is a graph showing variation of brightness with papillary dermis thickness for primaries 1 and 2, as described hereinabove.

The thickness of the papillary dermis may be obtained by utilising the property of human skin to vary its absorption of infrared radiation with varying papillary dermis thickness. In general, there is an inverse relationship between absorption and thickness. The fact that infrared radiation is also absorbed by other materials within the skin, particularly melanin and blood, is a complicating factor. However the effect on absorption of varying blood and melanin content is far smaller than the effect of papillary dermis thickness, and so the latter may still be measured. This can be done by obtaining two infrared images, each at a different wavelength. The chosen wavelengths are not important, but one should be further into the infrared (ie at longer wavelength) than the other. Suitable wavelength bands are 800–1000 nm and 600–800 nm, in that readily available infrared films and filters may be used. The brightness of points within the image obtained at the longer wavelength is affected to a greater extent by variations in the papillary dermis thickness. Conversely, the image obtained at shorter wavelength will be affected to a greater extent by other materials such as melanin and blood. By predicting the brightnesses of points of differing papillary dermis thickness and amounts of epidermal melanin which absorb near-infrared radiation at the two different infrared wavelengths, a reference graph (FIG. 1) can be obtained which consists of lines of constant papillary dermis thickness, wherein Primary 1 is the measurement made at the longer (800–1000 nm) wavelength and Primary 2 is the measurement made at the shorter (600–800 nm) wavelength. The absorption of blood within these wavelengths is very small (a hundredth of its peak value for visible wavelengths at 600–800 nm and even less for 800–1000 nm) and to a first approximation may be ignored. The presence of dermal melanin does introduce a small error in the range of low values for both primaries, but this is insignificant in practice. Thus, by comparing values obtained at these wavelengths with this graph, it is possible to ascertain the papillary dermis thickness. However it is within the scope of the present invention to measure brightness at such a long infra-red wavelength eg. 1100 nm that the brightness would vary to such a negligible extent with melanin and blood content that it would effectively depend solely on the papillary dermis thickness. This would also reduce the error introduced by the presence of dermal melanin. In such a case only one set of brightness measurements would be required. Furthermore, a transformation can be calculated which allows an image of the skin to be created which represents how the skin would appear if it had a papillary dermis thickness of any predetermined value.

In a preferred embodiment, the reference colour coordinate range for normal skin at the predetermined papillary dermis thickness is obtained as disclosed in the above-mentioned Technical Report as a curved surface lying within a three-dimensional colour space, with one of the bounding axes relating to the amount of melanin within the epidermis and the other relating to the amount of blood within the dermis. When an area containing dermal melanin is located, i.e. points do not lie on the normal colour surface, the epidermal melanin value within this area is estimated by either reference to the reference colour coordinate range for normal skin within regions identified as normal, or by reference to the epidermal melanin levels calculated within normal regions adjacent to said area containing dermal melanin. This value is then used with the corrected colour coordinates of the abnormal region at the same predetermined papillary dermis thickness to compute invasion depth and concentration of dermal melanin. The corrected skin colour coordinates for the area of skin under investigation may be calibrated to values equivalent to zero epidermal melanin. Instead of using LMS colour space, it is possible to use any other colour space, for example, the RGB colour space or a UV G IR colour space.

The dermis contrasts strongly in structure to that of the epidermis, being highly vascular, containing many sensory receptors and being made largely from collagen fibres to provide the essential structure of the skin. Between the epidermis and the dermis, the junction presents an extremely uneven boundary with finger-like dermal protrusions called dermal papillae projecting towards the skin surface. The dermis can be split into two further histologically distinct layers, the papillary dermis and the reticular dermis within which the structure of the collagen fibres differs significantly. The papillary dermis is situated directly below the epidermis and within which the collagen exists as a fine network of fibres. This is in contrast with the reticular dermis where the collagen fibres are aggregated into thick bundles which are arranged nearly parallel to the skin surface. In the case of melanin invasion of the papillary dermis, there is a layer containing blood, melanin and collagen, a layer containing either blood and collagen or melanin and collagen, depending upon whether melanin has passed the blood layer; and a layer containing just collagen. The different thicknesses of these layers, the amount of blood and the concentration of dermal melanin along with the amount of melanin in the overlying epidermis affect the remitted light. This can be modelled by calculating the net effect of these three layers for the differing parameters outlined.

A mathematical model describing the optics of the skin has been described in the above mentioned Symon D'O Cotton's Technical Report, whose disclosure has been included herein by reference, and this model can be extended to predict coloration of skin containing dermal descent of melanin.

Figure 2:
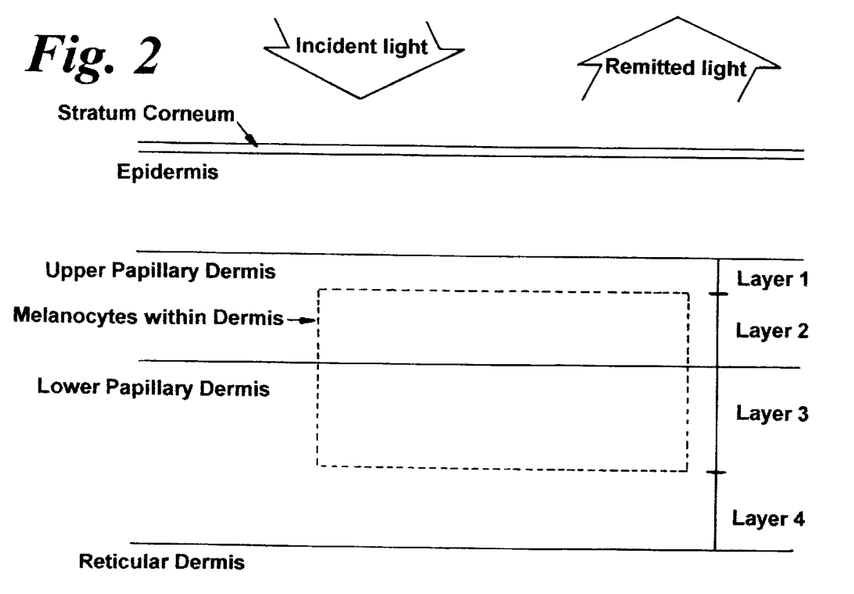
FIG. 2 is a schematic cross-sectional view through a section of skin illustrating melanin descent into the papillary dermis.

As can be seen from FIG. 2, there are now four distinct layers within the dermis which can combine to construct a simple model, 1) a layer within the upper papillary dermis containing no melanin, 2) a layer within the upper papillary dermis containing melanin, 3) a layer within the lower papillary dermis containing melanin, 4) a layer within the lower papillary dermis containing no melanin.

It should also be noted that the condition of melanin existing up to the dermo-epidermal junction is facilitated by allowing the thickness of layer 1 to be zero and likewise melanin can exist up to the papillary-reticular dermis boundary by setting the thickness of layer 4 to be zero.

In computing a model to predict this coloration it is useful to make note of the fact that, as discussed in section 2.1 of the Technical Report, the amount of back scatter due to melanin can be considered negligible. Therefore, in the same manner that it was possible to apply the Kubelka-Munk theory to the papillary dermis (section 3.2.2 of the Technical Report), to compute the coloration of sections of papillary dermis containing blood, where the back scattering component of blood was considered negligible, it is possible to compute the coloration of sections containing melanin. In this situation $\zeta(\lambda)$ (scattering coefficient) remains dependent only on wavelength whilst $\alpha$ (fraction of radiation absorbed per unit path length) becomes $\alpha(\lambda,\rho,\Phi)$ where $\Phi$ represents the density of dermal melanin within that layer. Further, following the proof given in equation (17) of the Technical Report, $\alpha$ $(\lambda,\rho,\Phi)$ can be shown to be the sum of $\alpha_{tv}(\lambda)$, $\alpha_b(\lambda)$ and $\alpha_m(\lambda)$, where $\alpha_m(\lambda)$ is the absorption coefficient of melanin. From the above it is possible to calculate R and T (diffuse radiation and transmission respectively). For simplicity of notation it is helpful to consider $R_1$ & $T_1$ where, $$R_1(\lambda,\rho,\Phi,d_n)=R(\beta(k(\alpha(\lambda,\rho,\Phi)),s(\zeta(\lambda))),K(k(\alpha(\lambda,\rho,\Phi)),s(\zeta(\lambda))).d_n)$$

and $$T_1(\lambda,\rho,\Phi,d_n)=T(\beta(k(\alpha(\lambda,\rho,\Phi)),s(\zeta(\lambda))),K(k(\alpha(\lambda,\rho,\Phi)), s(\zeta(\lambda))).d_n)$$

where $d_n$ is the layer thickness.

As was shown in section 3.2.3 of the Technical Report, two-layer systems can be combined to produce the total remitted and transmitted light for the dermis resulting in equation (20) of the Technical Report.

This can be simplified using the geometric series $$a + ar + ar^2 + ar^3 + \cdots = \frac{\alpha}{1-r} \text{ if } -1 < r < 1$$

to $$R_{1total}(\lambda, \rho_{ud}, \rho_{ld}, d_{ud}, d_{ld}) =$$
$$R_{1ud}(\lambda, \rho_{ud}, d_{ud}) + \frac{(T_{1ud}(\lambda, \rho_{ud}, d_{ud}))^2 R_{1ld}(\lambda, \rho_{ld}, d_{ld})}{1 - R_{1ud}(\lambda, \rho_{ud}, d_{ud}) R_{1ld}(\lambda, \rho_{ld}, d_{ld})}$$

Similarly, $T_{1total}$ can be shown to be $$T_{1total}(\lambda, \rho_{ud}, \rho_{ld}, d_{ud}, d_{ld}) = \frac{T_{1ud}(\lambda, \rho_{ud}, d_{ud}) * T_{1ld}(\lambda, \rho_{ld}, d_{ld})}{1 - R_{1ud}(\lambda, \rho_{ud}, d_{ud}) R_{1ld}(\lambda, \rho_{ld}, d_{ld})}$$

These equations can be extended, as is shown by Wan et al, [1981], to an n layered system resulting in values for $R_{12\ldots n}$ and $T_{12\ldots n}$ of $$R_{12\ldots n} = R_{12\ldots n-1} + \frac{T^2_{12\ldots n-1} R_n}{1 - R_{12\ldots n-1} R_n}$$

-continued $$T_{12...n} = \frac{T_{12...n-1}T_n}{1 - R_{12...n-1}R_n}$$

This system of equations can therefore compute the total remitted and transmitted light from an n layered system of arbitrary complexity provided that the thickness and composition of the layers is specified.

For the four-layer system shown in FIG. 2, this results in a value for the total light remitted and transmitted from the dermis dependent on $\lambda$, $P_{ud}$, $P_{ld}$, $d_{ud}$, $d_{ld}$, $d_{l2}$, $\Phi_{l2}$, $d_{l3}$ and $\Phi_{l3}$ where $d_{l2}$ and $d_{l3}$ are the thickness of layers 2 and 3 whilst $\Phi_{l2}$ and $\Phi_{l3}$ are their corresponding melanin densities. The thickness of layer 1 and layer 2 do not need to be explicitly defined as they are simply $d_{ud}$–$d_{l2}$ and $d_{ld}$–$d_{l3}$ respectively; similarly $\Phi_{l1}$ and $\Phi_{l4}$ are zero by definition. A further simplification is possible if it is assumed that $\Phi_{l2}$=$\Phi_{l3}$ leading to a single value of $\Phi$ for the dermis.

The results of these equations can be combined with the predicted light transmitted by the epidermis in the same manner as that discussed in section 3.3 of the Technical Report, thus leading to the following description of total remitted, $S_{rd}$, and transmitted $S_{td}$.

$S_{rd}(\lambda,\rho_{ud},\rho_{ld},d_{ud},d_{ld},d_{l2},d_{l3},\Phi,d_m)=$ $R_{2total}(\lambda,\rho_{ud},\rho_{ld},d_{ud},d_{ld},d_{l2},d_{l3},\Phi)\theta(\lambda,d_m)^2 S(\lambda)$ $S_{td}(\lambda,\rho_{ud},\rho_{ld},d_{ud},d_{ld},d_{l2},d_{l3},\Phi,d_m)=$ $T_{2total}(\lambda,\rho_{ud},\rho_{ld},d_{ud},d_{ld},d_{l2},d_{l3},\Phi)\theta(\lambda,d_m)^2 S(\lambda)$ These can be used to predict the value of the corresponding LMS primaries $$L(\rho_{ud}, \rho_{ld}, d_{ud}, d_{ld}, d_{l2}, d_{l3}, \Phi, d_m) =$$

$$\int_0^\infty R_{2total}(\lambda, \rho_{ud}, \rho_{ld}, d_{ud}, d_{ld}, d_{l2}, d_{l3}, \Phi)\theta(\lambda, d_m)^2 S(\lambda) S_L(\lambda) d\lambda$$

$$M(\rho_{ud}, \rho_{ld}, d_{ud}, d_{ld}, d_{l2}, d_{l3}, \Phi, d_m) =$$

$$\int_0^\infty R_{2total}(\lambda, \rho_{ud}, \rho_{ld}, d_{ud}, d_{ld}, d_{l2}, d_{l3}, \Phi)\theta(\lambda, d_m)^2 S(\lambda) S_M(\lambda) d\lambda$$

$$S(\rho_{ud}, \rho_{ld}, d_{ud}, d_{ld}, d_{l2}, d_{l3}, \Phi, d_m) =$$

$$\int_0^\infty R_{2total}(\lambda, \rho_{ud}, \rho_{ld}, d_{ud}, d_{ld}, d_{l2}, d_{l3}, \Phi)\theta(\lambda, d_m)^2 S(\lambda) S_S(\lambda) d\lambda$$

A further generalisation can be made to any primary, $P_{ni}$ leading to the following equation where $S_n$ defines the spectral response of that primary.

$$P_n(\rho_{ud}, \rho_{ld}, d_{ud}, d_{ld}, d_{l2}, d_{l3}, \Phi, d_m) =$$

$$\int_0^\infty R_{2total}(\lambda, \rho_{ud}, \rho_{ld}, d_{ud}, d_{ld}, d_{l2}, d_{l3}, \Phi)\theta(\lambda, d_m)^2 S(\lambda) S_L(\lambda) d\lambda$$

This equation can then be used to generate the expected coloration of human skin exhibiting dermal descent of melanin.

The result of this analysis is that it is possible for the same coloration to result from different combinations of the above parameters. This complicates the measurement of the dermal invasion of melanin, (but not identifying the presence of any dermal melanin). Indeed, to obtain this measurement, it is necessary to know the amount of melanin in the overlying epidermis. However, at points where dermal invasion has taken place, this parameter is difficult to determine simply by comparing colour coordinates of the abnormal location with colour coordinates for healthy skin. It is for this reason that, in the present invention, regions where dermal melanin exists are identified by reference to a reference colour coordinate range for healthy skin, and then the colour coordinates of these regions are compared with the colour coordinates at one or more normal skin locations. If said normal skin locations are adjacent to the region where dermal melanin exists, it is sufficient to use the epidermal melanin levels calculated for such normal skin locations to estimate the epidermal melanin levels at the region where dermal melanin exists Alternatively, it is possible to perform a measurement of the epidermal melanin levels within areas of the skin where the presence of dermal melanin has been identified, by assessing the deviation in coloration at the blue end of the spectrum, from the reference colour coordinate range for normal skin due to the presence of such dermal melanin. At the blue end of the spectrum, the increase in such deviation quickly slows with increasing depth of melanin penetration until a "saturation point" is reached. By assuming that the depth of melanin penetration within the dermis is large enough for such saturation to have occurred, an estimate of the deviation from the reference colour coordinate range for normal skin can be made. This estimate allows a calculation to be made of the skin coloration assuming no dermal melanin, and therefore by reference to the colour coordinate range for normal skin, of the level of epidermal melanin. It is within the scope of the present invention to measure the epidermal melanin levels directly, for example using polarised light, and to incorporate such measurements in the measuring step (ii) above.

By any of the above methods, the effect of what would have been the normal epidermal melanin level in the abnormal skin location can be taken into account, thereby enabling a more accurate determination of melanin descent By comparing the values of the skin image represented in a certain colour space with theoretically calculated values covering all possible amounts of blood, dermal melanin penetration and melanin concentration within the same colour space, the values of those three parameters can be obtained for every point in the image. Since the papillary dermis thickness and epidermal melanin content are known, it is possible to compute a detailed three-dimensional reconstruction of the top layers of human skin. This is of great potential interest to the medical profession and enables routine examination of the internal structure of living skin, just as X-rays, NMR and ultrasound are used for examining other parts of the body. It is also within the scope of the invention to acquire the infra-red and/or visible images using lasers of different wavelengths or by using spectral analysis.

It is possible to use a computer programmed with the above algorithms to perform the actual calculations. However, before these calculations can be performed, an image of the area of skin under investigation must be represented in the same colour space as for the normal skin reference colour coordinate range. This can be done in a number of ways. In one way, the skin colour coordinates are acquired from an image using the same lighting conditions and a CCD camera calibrated in the same way as that used to produce the healthy skin reference colour coordinate range. Alternatively, if exactly the same lighting conditions are not used, a white standard or other appropriate correction factor can be used to allow callibration of the image within the software. As a further alternative, a colour image can be acquired using a colour photographic film which is then digitised. This can be performed using either exactly the same lighting conditions and a calibrated set-up or again with the inclusion of a white standard or other appropriate correction factor. It is within the scope of this invention to obtain both the infra-red and visible images with a single digital camera or to calculate the value of the necessary primaries through the use of spectroscopy.

The present invention will now be described in further detail and with reference to the accompanying drawings, in which.

Figure 3:
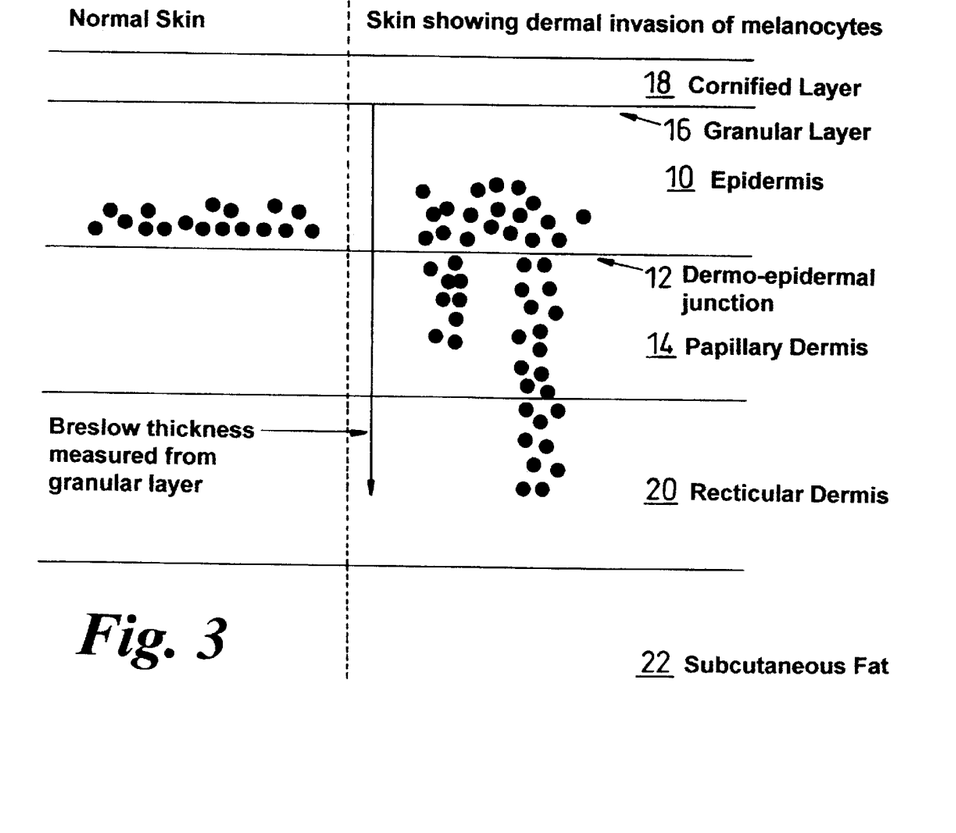
FIG. 3 is a schematic cross-sectional view through a section of skin illustrating normal, healthy regions and an abnormal region where, in this case, melanin descent into the papillary dermis and the reticular dermis has taken place.

Referring now to FIG. 3 of the drawings, a schematic skin section is shown wherein melanin (indicated by the black circles in FIG. 3) in normal healthy skin are present in the lower part of epidermis 10 adjacent but above the dermo-epidermal junction 12 between the epidermis and the papillary dermis 14. The Breslow thickness referred to above is the depth of melanin invasion in millimeters measured from granular layer 16 which is a layer in the epidermis 10 where the skin goes scay and forms the tough outer cornified layer 18. In the abnormal region of the skin, the melanin is shown as having descended not only into the papillary dermis 14, but also into the underlying reticular dermis 20 lying above the subcutaneous fat layer 22. It is to be appreciated that, in other cases, melanin decent can be into any layer of the skin and may even be into the subcutaneous fat layer 22.

Figure 4:
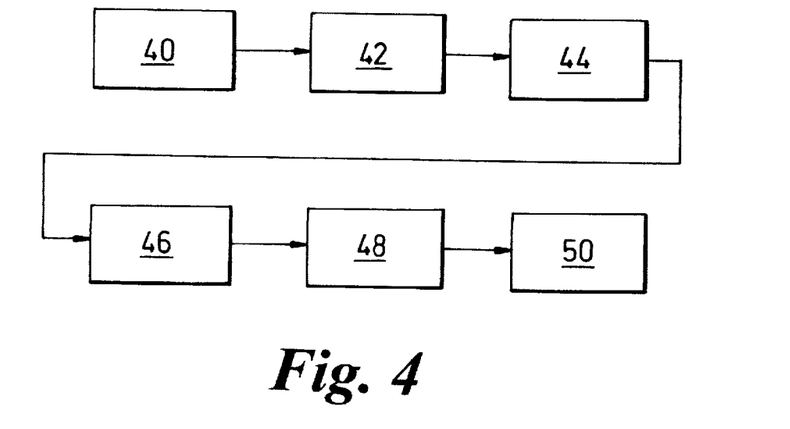
FIG. 4 is a block diagram showing the steps involved in one embodiment of the method of the present invention.

Referring now to FIG. 4, there is shown a block diagram illustrating the steps involved in a typical method of measurement in accordance with the present invention. In FIG. 4, block 38 exemplifies method step (i) above-the determination of papillary dermis thickness by shining infrared light at two wavelengths on an area of skin being subjected to measurement and measuring the amount of light reflected from a plurality of points within that area. Block 40 exemplifies method step (ii) above-the acquisition of an image at visible wavelengths of the same skin area. This can be by CCD camera, digitised film or any other convenient means. Block 42 exemplifies method step (iii) above-the transformation of the image into corrected colour space of the skin model at a predetermined papillary dermis thickness. Block 44 exemplifies method steps (iv and v) above-the identification of regions containing dermal melanin, by comparing the corrected skin colour coordinates with the reference colour coordinate range. Block 46 exemplifies method step (vi) above-use of the corrected colour space to calculate the amounts of epidermal melanin within normal regions adjacent to the regions containing dermal melanin and use thereof to give an indication of the amounts thereof which exist in the regions containing dermal melanin. Block 48 exemplifies a first part of method step (vii) above-calculation of dermal invasion using the measured coloration of the abnormal regions and the calculated amount of epidermal melanin from 46. Block 50 exemplifies a second part of method step (vii) above-transformation of the calculated dermal invasion of melanin into either the Breslow thickness or the Clark's level of invasion. This can be reported as either representing the maximum invasion or as an image showing invasion over the skin.

Figure 5:
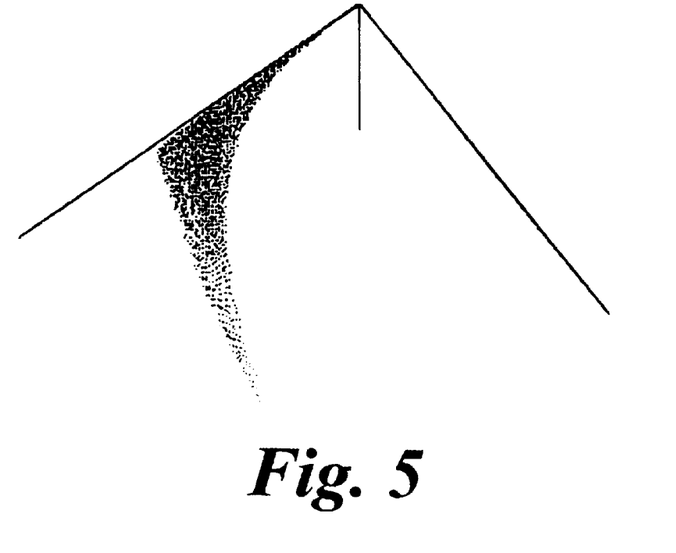
FIG. 5 is a diagram showing the predicted surface of normal skin coloration within a three-dimensional colour space.

Referring now to FIG. 5, the shaded surface indicates the range of colorations which can exist in normal healthy skin corrected to the predetermined papillary dermis thickness. Skin colorations which depart from this surface are indicative of dermal melanin.

Figure 6:
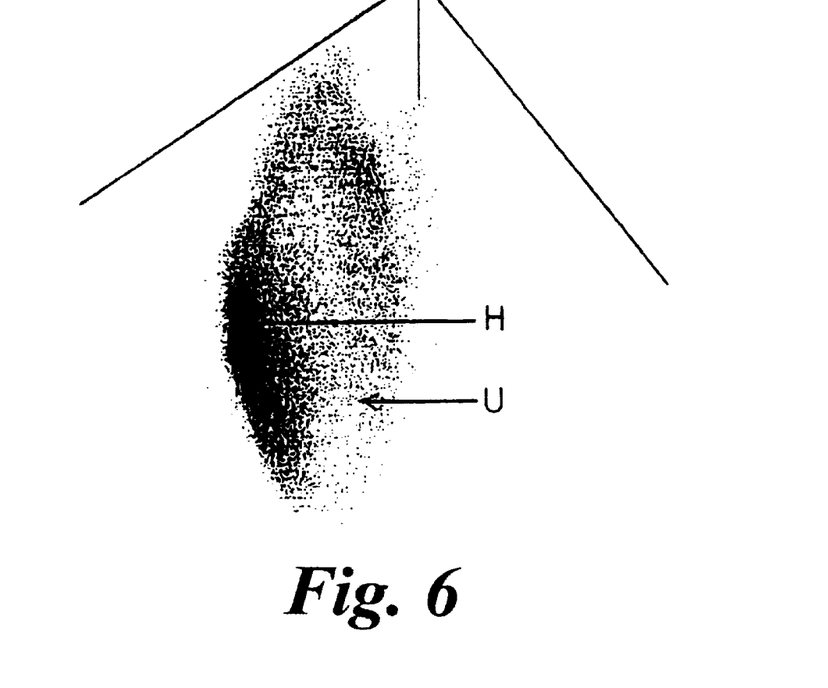
FIG. 6 is a diagram showing coloration within the skin cancer that is shown in FIG. 7 in the same 3-D colour space as depicted in FIG. 5, wherein areas of normal and abnormal coloration are shown.
Figure 7:
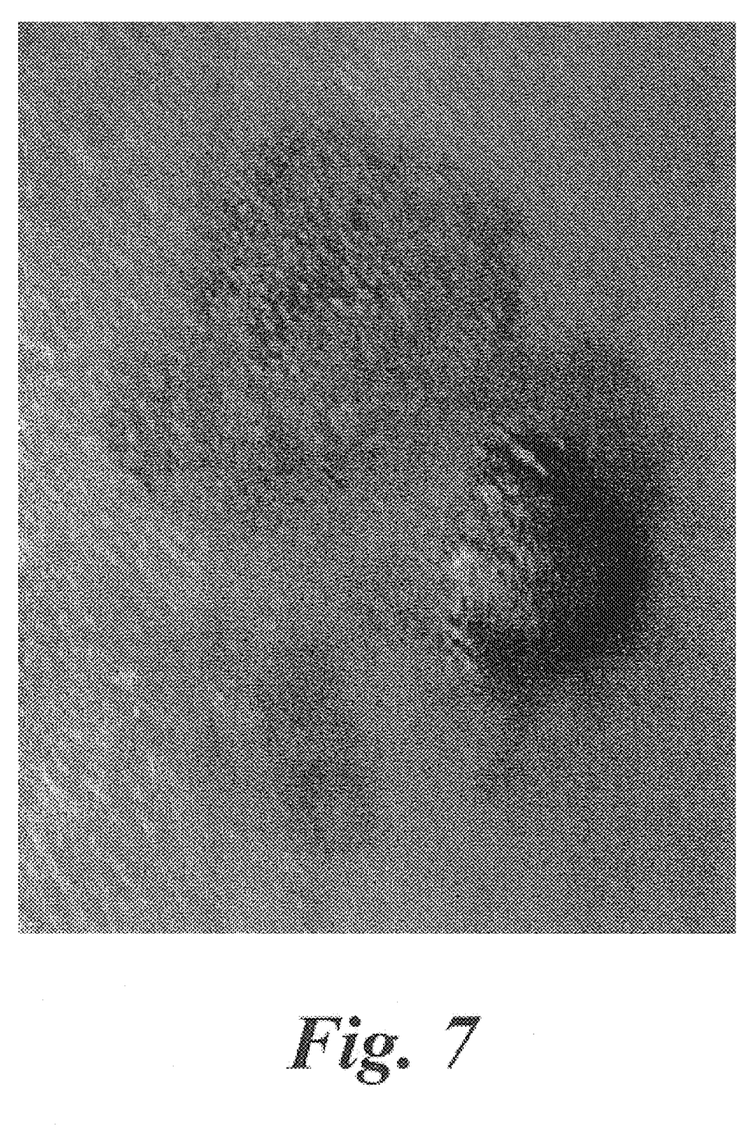
FIG. 7 is a photographic image of the skin cancer.

Referring now to FIGS. 6 and 7, it can be seen that a region of the skin which is shown in FIG. 7 and which is indicated by arrow H in FIG. 6 lies at a position corresponding to part of the shaded surface illustrated in FIG. 5 and is indicative of normal healthy skin, whereas an adjacent region indicated by arrow U in FIG. 6 lies outside such surface and is indicative of skin containing dermal melanin. Comparison of the coloration of these two adjacent regions H and U enables the depth of melanin invasion in the abnormal region of the skin in FIG. 7 to be computed.

What is claimed is:

1. A method of non-invasively analysing skin structure, comprising the steps of:
   (i) measuring radiation having a wavelength within a wave band extending from 600 nm and into infrared from at least one location in an area of skin under investigation so as to give an indication of papillary dermis thickness over said area;
   (ii) measuring skin colour co-ordinates at said at least one location in said area of skin;
   (iii) using data obtained in measuring steps (i) and (ii) to calculate corrected skin colour co-ordinates over said area which correspond to a predetermined papillary dermis thickness, and;
   (iv) comparing the corrected skin colour co-ordinates obtained in step (iii) with a reference colour co-ordinate range for healthy skin of said the same predetermined papillary dermis thickness.

2. A method according to claim 1, comprising the additional steps of;
   (v) identifying an abnormal location within said area of skin where the corrected skin colour co-ordinates lie outside the reference colour co-ordinate range; (vi) calibrating the corrected skin colour co-ordinates of said abnormal location with the corrected skin colour co-ordinates' of at least one skin location having colour co-ordinates lying within said reference colour co-ordinate range for normal skin, and;
   (vii) using the skin colour co-ordinates to assess a degree of abnormality of said abnormal skin location.

3. A method according to claim 2, wherein an independent measurement is made of epidermal melanin level.

4. A method according to claim 3, wherein said independent measurement of epidermal melanin level is by polarized light.

5. A method according to claim 2, wherein said calibration in step (vi) includes estimating epidermal melanin level in said abnormal location by reference to epidermal melanin levels calculated within at least one normal skin location adjacent said abnormal region.

6. A method according to claim 2, wherein said calibration in step (vi) includes measuring epidermal melanin levels at said abnormal location by assessing any deviation at the blue end of the spectrum at said abnormal location from the reference colour co-ordinate range for normal skin.

7. A method according to claim 2, wherein step (i), a single infrared image at a wavelength of greater than about 1100 nm is obtained for each of said locations.

8. A method according to claim 2, wherein in step (i) two images, each at a different wavelength, are obtained for each of said locations, whereby to enable the effect of any epidermal melanin and dermal blood present to be accounted for in the calculation of step (iii).

9. A method according to claim 8, wherein said wavelengths fall within wavelength bands of 800–1000 nm and 600–800 nm respectively.

10. A method according to claim 2, wherein the skin colour coordinates of step (ii) are acquired from an image using different lighting conditions than used to obtain the healthy skin reference colour coordinate range, and a white standard or other correction factor is used to allow calibration of the image with the reference colour coordinate range.

11. A method according to claim 1, wherein an independent measurement is made of epidermal melanin level.

12. A method according to claim 11, wherein said independent measurement of epidermal melanin level is by polarized light.

13. A method according to claim 1, wherein step (i), a single infrared image at a wavelength of greater than about 1100 nm is obtained for each of said locations.

14. A method according to claim 1, wherein in step (i) two images, each at a different wavelength, are obtained for each of said locations, thereby to enable the effect of any epidermal melanin or dermal blood present to be accounted for in the calculation of step (iii).

15. A method according to claim 14, wherein said wavelengths fall within wavelength bands of 800–1000 nm and 600–800 nm respectively.

16. A method according to claim 14, wherein said infrared image(s) is or are obtained using infrared photographic film, or laser(s) or by spectral analysis.

17. A method according to claim 1, wherein the reference colour coordinate range for normal skin at the predetermined papillary dermis thickness referred to in step (iv), is obtained as a curved surface lying within a three-dimensional colour space, with a first bounding axis relating to the amount of melanin within the epidermis and a second bounding axis relating to the amount of blood within the dermis.

18. A method according to claim 17, wherein said three-dimensional colour space is selected from LMS, RG5 and UV G IR colour spaces.

19. A method according to claim 1, wherein the skin colour co-ordinates of step (ii) are acquired from an image using lighting conditions and a calibration set-up which are the same as lighting conditions and a calibration set-up used to produce the healthy skin reference colour co-ordinate range.

20. A method according to claim 1, wherein the skin colour coordinates of step (ii) are acquired from an image using different lighting conditions than used to obtain the healthy skin reference colour coordinate range, and a white standard or other correction factor is used to allow calibration of the image with the reference colour coordinate range.

21. An apparatus for non-invasively analysing skin structure, comprising:

a projector for projecting radiation having a wavelength within a wave band extending from 600 nm and into infrared onto an area of skin under investigation;

measuring means for measuring remitted radiation from at least one location over an area of skin under investigation so as to give an indication of papillary dermis thickness over said area;

skin colour co-ordinate measuring means for measuring skin colour co-ordinates at said at least one location over said area of skin;

calculating means for using data obtained in measuring steps (i) and (ii) to calculate corrected skin colour co-ordinates over said area which correspond to a predetermined papillary dermis thickness, and;

colour comparison means for comparing corrected skin colour co-ordinates obtained in step (iii) with a reference colour co-ordinate range for healthy skin of said predetermined papillary dermis thickness.

* * * * *

UNITED STATES PATENT AND TRADEMARK OFFICE
CERTIFICATE OF CORRECTION

PATENT NO. : 6,324,417 B1
DATED : November 27, 2001
INVENTOR(S) : Symon D'Oyly Cotton It is certified that error appears in the above-identified patent and that said Letters Patent is hereby corrected as shown below:

Title page, Item [63] and Column 1, line 4,
Related U.S. Application Data, delete "PCT/GB97/03117" and insert in its place -- PCT/GB97/03177 --.

Title page,
Item [56], OTHER PUBLICATIONS, "Clark et al." reference, delete "behavioar" and insert in its place -- behaviour --.

Signed and Sealed this

Twenty-first Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,324,417 B1
DATED        : November 27, 2001
INVENTOR(S)  : Symon D'Oyly Cotton It is certified that error appears in the above-identified patent and that said Letters Patent is hereby corrected as shown below:

<u>Title page,</u>
Item [73], Assignee, delete "Optiscan Limited" (GB) and insert in its place
-- Astron Clinica Limited (GB) --.

Signed and Sealed this

Sixteenth Day of March, 2004

JON W. DUDAS
*Acting Director of the United States Patent and Trademark Office*